US009962405B2

(12) United States Patent
Sahin et al.

(10) Patent No.: US 9,962,405 B2
(45) Date of Patent: May 8, 2018

(54) ANTIVIRAL GEL COMBINATION

(71) Applicant: YEDITEPE UNIVERSITESI, Istanbul (TR)

(72) Inventors: Fikrettin Sahin, Istanbul (TR); Selami Demirci, Istanbul (TR); Aysegul Dogan, Istanbul (TR); Ayla Burcin Asutay, stanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 0 days. days.

(21) Appl. No.: 14/783,428

(22) PCT Filed: Apr. 7, 2014

(86) PCT No.: PCT/TR2014/000105
§ 371 (c)(1),
(2) Date: Oct. 8, 2015

(87) PCT Pub. No.: WO2014/168592
PCT Pub. Date: Oct. 16, 2014

(65) Prior Publication Data
US 2016/0058790 A1   Mar. 3, 2016

(30) Foreign Application Priority Data
Apr. 8, 2013   (TR) ............... a 2013 04210

(51) Int. Cl.
| A61K 33/22  | (2006.01) |
| A61K 31/205 | (2006.01) |
| A61K 9/06   | (2006.01) |
| A61K 47/32  | (2006.01) |
| A61K 31/155 | (2006.01) |
| A61K 47/10  | (2017.01) |

(52) U.S. Cl.
CPC ............... *A61K 33/22* (2013.01); *A61K 9/06* (2013.01); *A61K 31/155* (2013.01); *A61K 31/205* (2013.01); *A61K 47/10* (2013.01); *A61K 47/32* (2013.01)

(58) Field of Classification Search
None
See application file for complete search history.

(56) References Cited

U.S. PATENT DOCUMENTS

| 4,285,934 A    | 8/1981 | Tinnell |
| 4,941,921 A *  | 7/1990 | Anic ............... C07C 215/08  127/33 |
| 2003/0165545 A1* | 9/2003 | Huth ............... A61K 9/1075  424/400 |
| 2007/0141091 A1 | 6/2007 | Xia |

FOREIGN PATENT DOCUMENTS

| CA | 2284345 A1    | 4/2001 |
| EP | 1666027 A1    | 6/2006 |
| EP | 1790349 A1    | 5/2007 |
| WO | WO2006025724 A1 | 3/2006 |

OTHER PUBLICATIONS

Riley Le: "Herpes simplex virus", Semin Perinatol, 1998, 22:284-292.
Siegel D, Golden E, Washington AE, Morse SA, Fullilove MT, Catania JA, Marin B. Hulley SB: "Prevalence and correlates of herpes simplex infections", JAMA, 1992, 268:1702-1708.
Guttula DS, Lakshmi AG: "Temperature triiggered in situ gelling system for ocular antiviral drug", 2011.
Taylor TJ., Brockman MA., McNamee EE., Knipe DM.: "Herpes simplex virus", Front. Biosci., 2002, 7: D752-D764.
Whitley RJ., Roizman B.: "Herpes simplex virus infections", Lancet, 2001, 357, 1513-8.
Wilhelmus KR.: "Antiviral treatment and other therapeutic interventions for herpes simplex virus epithelial keratitis", Cochrane Database Syst Rev, 2010, 12, 1-21.
Choong K, Walker NJ, Apel AJG, Whitby M: "Aciclovir resistant herpes keratitis", Clin. Experiment.Ophthalmol., 2010,38, 309.
Safrin S, Kemmerly S, Plotkin B; "Foscarnet-resistant herpes simplex. virus infection in patients with AIDS", J Infect Dis, 1994, 169:193-6.
Duan R, De Vries RD, Osterhaus AD, Remeijer L, Verjans GM: "Acyclovir-resistant corneal HSV-1 isolates from patients with herpetic keratitis", J Infect Dis, 2008, 198: 659-63.
Trousdale MD, Nesbum AB, Miller CA: "Assessment of acyclovir on acute ocular infection induced by drug-resistant strains of HSV-I", Invest Ophthabnol Visual Sci, 1981, 20: 230-5.
Lawrence, J.R., Zhu, B., Swerhone, G.D.W., Topp, E., Roy, J., Wassenaar, L.I., Rema, T., Korber, D.R.: "Community-level assessment of the effects of the broad-spectrum antimicrobial chlorhexidine on the outcome of river microbial biofilm development", Applied and Environmental Microbiology, 2008, 74 (11), 3541-3550.
Park JB, Park NH: "Effect of chlorhexidine on the in vitro and in vivo herpes simplex virus infection", Oral Surg, 1989, 67: 149-153.
Park JB, Park NH, Min BM: "Combined synergistic antiherpetic effect of acyclovir and chlorhexidine in vitro", Oral Surg Oral Med Oral Pathol, 1991, 71:193-96.
Benderdour M, Van Bui T, Hess K, Dicko A, Belleville F, Dousset B: "Effects of boron derivatives on extracellular matrix formation", J Trace Elem Med Biol 2000: 14: 168-173.
Bailey PJ., Cousins G., Snow GA., White AJ.: "Boron-Containing Antibacterial Agents: Effects on Growth and Morphology of Bacteria Under Various Culture Conditions", Antimicrobial Agents and Chemotherapy, 1980, 17, 549.

(Continued)

*Primary Examiner* — Jake Vu
(74) *Attorney, Agent, or Firm* — Gokalp Bayramoglu

(57) ABSTRACT

The present invention relates to an antiviral gel combination. The said gel is composed of a boron compound, and the poloxamer and chlorhexidine compounds; and the gel obtained with the present invention demonstrates high activity on Herpes Simplex Type 1 Virus (HSV).

6 Claims, 1 Drawing Sheet

(56) References Cited

OTHER PUBLICATIONS

Benkovic SJ., Baker SJ., Alley M.R.: "Identification of borinic esters as inhibitors of bacterial cell growth and bacterial methyltransferases", CcrM and MenH, Journal of Medicinal Chemistry, 2005, 48, 7468-7476, 2005.

Qin G., Tian S., Chan Z., Li B.: "Crucial role of antioxidant proteins and hydrolytic enzymes in pathogenicity of Penicillium expansum", Molecular & Cellular Proteomics, 2007, 6, 425-438, 2007.

Qin G., Zong Y., Chen Q., Hua D., Tian S.: "Inhibitory effect of boron against Botrytis cinerea on table grapes and its possible mechanisms of action", International Journal of Food Microbiology, 2010, 138, 145-150.

Batrakova, EV. and Kabanov AV.: "Pluronic Block Copolymers: Evolution of Drug Delivery Concept from Inert Nanocarriers to Biological Response Modifiers", J Control Release, 2008, 10, 130(2), 98-106, Sep. 2008.

Kabanov, A., Nazarova I., Astafieva I., Batrakova E., Alakhov V., Yaroslavov A., Kabanov V.: Micelle formation and solubilization of fluorescent probes in poly (oxyethylene-b-oxypropilene-boxyethylene) solutions, Macromolecules, 1995, 28, 2303-2314.

Ramirez, O.T. Mutharasan R.: "The role of the plasma membrane fluidity on the shear sensitivity of hybridomas grown under hydrodynamic stress", Biotechnol. Bioeng, 1990, 36, 911-920.

Lalitha, MK. and Vellore TN.: "Manual on antimicrobial susceptibility testing", URL: http://www.ijmm.org/documents/Antimicrobial.doc, 2005.

Yalvac: M.E., Ramazanoglu M. et al: "Comparison and optimisation of transfection of human dental follicle cells", a novel source of stem cells, with different chemical methods and electro-poration, Neurochem Res, 2009, 34(7): 1272-7.

Markland, W., McQuaid, T. J., Jain, J., Kwong, A. D.: "Broad-Spectrum Antiviral Activity of the IMP Dehydrogenase Inhibitor VX-497: a Comparison with Ribavirin and Demonstration of Antiviral Additivity with Alpha Interferon", Antimicrob. Agents Chemother., 2000, 44 (4): 859.

Demina N B et al: "Contact lens maintenance systems", Pharmaceutical Chemistry Journal, Springer New York LLC, vol. 35, No. 2, Jan. 1, 2001, pp. 114-119, XP002481617.

De Oliveira D P et al: "In Vitro Assessment of a Gel Base Containinng 2% Chlorhexidine as a Sodium Perbarate's Vehicle for Intracoronal Bleaching of Discolored Teeth", Journal of Endodontics, Lippincott Williams & Wilkins, Philadelphia, vol. 32, No. 7, Jul. 1, 2006, pp. 672-674, XP024991872.

Batts A H et al: "The effect of some preservatives used in nasal preparations on the mucus and ciliary components of mucociliary clearance", Journal of Pharmacy and Pharmacology, John Wiley & Sons LTD, vol. 42, No. 3, Mar. 1, 1990, pp. 145-151, XP009180007.

Fry R S et al: "Effect of dietary boron on physiological responses in growing steers inoculated with bovine herpesvirus type-1", Research in Veterinary Science, British Veterinary Association, vol. 90, No. 1, Feb. 1, 2011, pp. 78-83, XP027584690.

\* cited by examiner

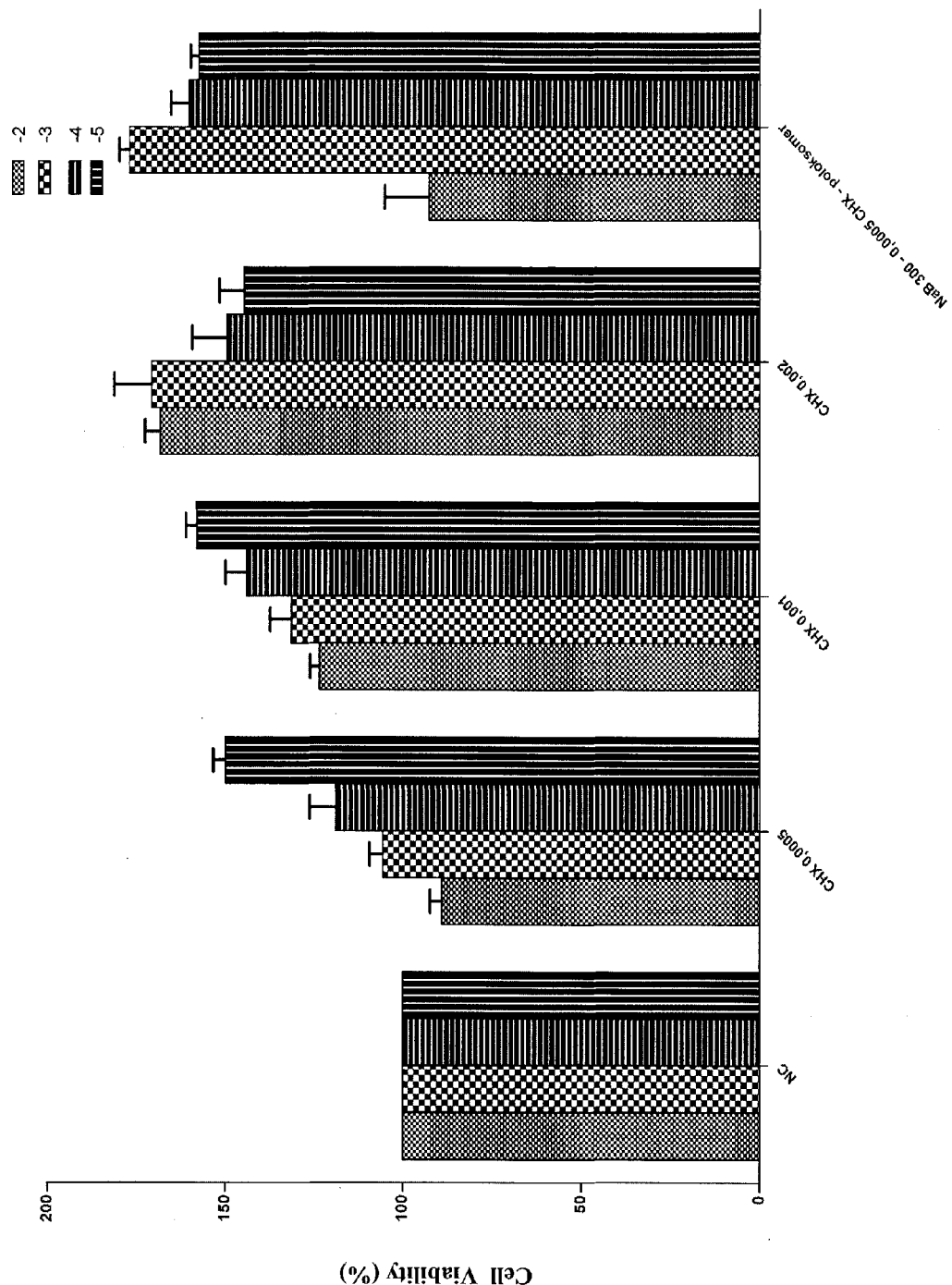

ANTIVIRAL GEL COMBINATION

TECHNICAL FIELD OF THE INVENTION

The present invention relates to an antiviral gel combination effective on Herpes Simplex Virus (HSV).

BACKGROUND

Herpes Simplex Virus (HSV) is an important human pathogen and a double strand DNA virus. This virus is classified according to different host species, replication cycle time, and its capacity to decompose the cell it infects. The current HSV has two different subtypes one of which infects the mucosal regions of the mouth, pharynx, lips and eyes (HSV-1) and the other of which causes genital system diseases which are sexually transmitted [1]. The incidence of infection, which is generally seen in children, varies according to geographical and socioeconomic conditions. The virus is transmitted by close contact and 90% of the children living in regions of low socioeconomic level are tested seropositive for HSV-1 [2]. In addition, according to American National Eye Institute (NEI), ocular herpes infection has been encountered in 400,000 reported cases in the United States and 50,000 new or repeating cases are encountered each year [3].

HSV infection, after causing vesicular lesions in mucosal epithelial cells, is transmitted to the sensory neurons and followed by a latent infection which may prolong throughout the life of the host [4]. Reactivation of the virus from latency causes recurrent diseases at or near the primary site of infection. The herpes caused by HSV-1 infection are generally not life threatening. However, cornea infection (keratitis), central nervous system infection (encephalitis), and infections in newborns and people having weak immune systems may cause serious diseases [5].

In today's technology, the variety of drugs used for HSV infections is limited. The most important of these drugs used in clinical practice are Acyclovir, Vidarabine, Cidofovir, Trifluridine, Brivudine and Foscarnet [6]. HSV types which are particularly resistant against Acyclovir, Vidarabine and Foscarnet drugs have developed due to the unconscious and continuous use of these anti-herpetic drugs [7-8-9-10]. However, the HSV types which have developed resistance against these drugs due to immune system deficiency particularly in individuals who have received chemotherapy treatment or organ transplant create serious problems in clinical applications. Because of these difficulties that are experienced and the fact that the drug variety in these therapeutic applications is limited, development of new prophylactic and anti-herpetic agents or making the existing systems more efficient has become an important area.

Chlorhexidine (1,1'-hexamethylene-bis[5-(p-chloro-phenyl)-biguanide; $C_{22}H_{30}C_{12}N_{10}2C_6H_{12}O_7$), which is a reliable and effective chemical in optimized concentrations, is used in gargles, gels and toothpastes in order to prevent dental plaque formation. With the studies conducted, it is observed that chlorhexidine has antimicrobial activity against many microorganism types (yeast, fungus, facultative anaerobe and aerobe bacteria) [11]. In addition to the antimicrobial properties of chlorhexidine, its antiviral activity against Herpes simplex virus is also shown by in vitro and in vivo studies [12]. In in vitro studies, it is determined that chlorhexidine inhibits viral replication of HSV-1 virus in vero cells. Additionally, it is proved in animal studies that chlorhexidine inhibits the virus from proliferating and forming lesions when topically applied on infected skin [13]. Again in the same study, it is determined that chlorhexidine alone has antiviral activity and that its combination with Acyclovir exhibits a synergistic effect. As a conclusion it is shown that the combination group significantly reduced viral replication more than the group to which Acyclovir was administered alone.

It has been known for over a century that boron is an important trace element for plants. It is stated in the studies conducted that this element plays important roles in proton and ion transfer, steroid hormone synthesis and release and in bone and calcium metabolism in animals and humans [14]. In the state of the art applications, antimicrobial activity of various boron compounds on bacterial [15-16] and fungal [17-18] species are demonstrated. It is reported that the formulation made with boric acid heals herpes when applied topically on humans [19].

The U.S. Pat. No. 4,285,934, an application in the state of the art, discloses that combination of boric acid (15%), tannic acid (15%) and salicylic acid (3%) is effective against herpes lesions.

The patent documents no. EP1790349 and WO2005-MX7920050902, other applications in the state of the art, disclose that sodium pentaborate pentahydrate can be used for treatment of viral and bacterial diseases by activating immune system. However it was not mentioned about any antiviral activity of these components on Herpes Simplex Virus and other viruses.

Another component which is pluronics, also known as poloxamer, are the synthetic polymers which have a triblock structure composed of hydrophobic polypropylene oxide and hydrophilic polyethylene oxide units [20]. These polymers are surfactant due to their amphiphilic structures and can interact with the cell membrane. Pluronics can be used in transportation of drugs as the amounts of micelle they form are more than the critical micelle concentration in the solutions [21]. Additionally, they can be used in bioreactors for enhancing cell viability and decreasing agitation stress [22]. Different components of poloxamers are used in nano-gel formulation. Thanks to mucoadhesive properties of these polymers, the drug can effectively penetrate into the cell and its efficacy can be enhanced by preventing decomposition thereof.

The United States patent document no. US2007/0141091, one of the applications known in the state of the art, discloses that poloxamer is added at a concentration of 1% (w/v) and it is used topically against infections.

SUMMARY OF THE INVENTION

An objective of the present invention is to provide an antiviral gel combination which is effective against HSV-1 virus.

Another objective of the present invention is to provide an antiviral gel combination which removes the deformation occurring in the area, where HSV-1 infection occurs, in a short period of time.

A further objective of the present invention is to provide an antiviral gel combination which kills the pain in the area, where HSV-1 infection occurs, in a short period of time.

BRIEF DESCRIPTION OF THE DRAWING

"An antiviral gel combination" developed to fulfill the objectives of the present invention is illustrated in the accompanying figure, in which:

FIG. 1 is the graphical representation of the antiviral activity of the components within the gel formulation (NC; Negative Control, CHX; Chlorhexidine, NaB; Sodium pentaborate pentahydrate).

DETAIL DESCRIPTION OF THE INVENTION

In the present invention, the anti-herpetic chlorhexidine is obtained by the combination of different concentrations of sodium pentaborate pentahydrate ($NaB_5O_8.5H_2O$) compound and poloxamer.

Experimental Study

Preparation of the Gel

In preparation of the gel of the present invention, first of all 3% glycerin (3 ml glycerin in 97 ml water) and 0.12-0.2 g/ml chlorhexidine were added to distilled water.

After preparing 1% (w/v) carbopol solution in the said prepared mixture, 1.6 gr 18% NaOH solution was added into a 1 liter carbopol-water mixture in order to enable gelation of carbopol and to neutralize pH.

1% carbopol in glycerin-water-chlorhexidine mixture was subjected to hydratation at room temperature. 0.5-5% boron compound (g/ml) and 0.3-5% poloxamer (g/ml) were added to the obtained mixture.

The mixture was stored at 4° C. for 16-24 hours and made ready for use. The gel obtained was subjected to experimental studies in its final form.

In the experimental study of the present invention, sodium pentaborate pentahydrate was used as the boron compound. Apart from this boric acid, alkaline and alkaline earth metal borates and all hydrates forms of these borates, ammonium borates, boric acid esters, which are among boron compounds, can also be used.

Characterization Study

Determining Cell Toxicity

Toxic effect of the prepared gel formulation is determined by using MTS method [24]. The molecules used in the gel were prepared alone or in combination in the medium and applied on the cell lines L929 (Mouse Fibroblast), HF (Human Fibroblast) and Vero (Green Monkey Kidney Cells) which were seeded onto the 96-well culture plates (5000 cells/well) by counting. The response of the cells to toxicity of the molecules was determined by measuring cell viability for 3 days. Cell viability was determined by using a method called MTS which measures mitochondrial dehydrogenase enzyme activity of the cell. The MTS substance added onto the cells together with the medium results in colored formazan crystals formation as an indicator of cell viability. The resulting color change was evaluated based on the absorbance measurement (490 nm) by using ELISA plate reader. The obtained values were analyzed using Microsoft Office Excel database.

Determination of Antiviral Activity

Antiviral activities of the active molecules and their combinations on HSV (Herpes Simplex) type 1 virus were determined as it was previously reported in the literature [25]. Whether these substances have toxic effect on Vero cells was determined by cell viability analyses. Antiviral analyses were completed upon adding 0.0005, 0.001 and 0.002% chlorhexidine concentrations, which were previously used in the literature, to the prepared gel formulation. Vero cells were seeded onto 96-well culture plates at a concentration of 5000 cells/well. After the cells completely settled, the next day, 7 different virus dilutions and active ingredient combinations, whose antiviral activity will be analyzed, were applied on the cells. Three days later, cell viability was shown by MTS experiment and viral inhibition was calculated.

Experimental Results

Vero cells and Herpes Simplex Type 1 virus were used in order to observe the activity of the antiviral gel formulation; which is composed of a mixture of sodium pentaborate pentahydrate chlorhexidine and poloxamer; on Herpes Simplex Type 1 virus. Virus stock dilutions were prepared and used for the analysis. Five different concentrations were prepared from the main stock up to $10^{-5}$ concentration and among these concentrations, the dilution of $10^{-1}$ concentration was cancelled since no viable cell was observed. The other antiviral analyses were made at four different concentration values ranging from $10^{-2}$ to $10^{-5}$. Chlorhexidine was applied at three different concentrations: 0.0005-0.001-0.002%.

In the applications made for chlorhexidine alone, the best antiviral activity was observed at an average concentration of 0.002%. However this concentration value is known to have cytotoxic effect [12].

Antiviral activity analyses were made by adding sodium pentaborate pentahydrate in amounts which are decided in accordance with the experiments conducted previously, to the prepared combinations. Cytotoxic effect of sodium pentaborate pentahydrate was determined by testing on vero cells prior to the antiviral analyses. The concentrations used in the experiments reached up to 300 µg/ml and no cytotoxic effect was observed.

High rate of antiviral activity was observed in the mixture prepared using 300 µg/ml sodium pentaborate pentahydrate, 0.0005% chlorhexidine, 5 mg/ml poloxamer at $10^{-4}$ and $10^{-5}$ concentrations, particularly at $10^{-3}$ viral dilution. According to the results, the highest antiviral activity is obtained by combination of these four molecules. This way, with the formulation prepared by combining four different molecules, chlorhexidine can be used at a level which will not be toxic to the cells and a product which has maximum antiviral activity can be formed (FIG. 1).

By application of the present invention, antiviral activity prevents viral replication and prevents proliferation of the virus by strengthening the immune system.

The combination of the present invention is suitable for use in many pharmacological areas such as applications of tablets, capsules, pastilles, drops, syrup, suppository, gel, lotion, ampoule, tube. The prepared combination can be administered by all kinds of ways that enable body absorption such as by oral, nasal, ophthalmic, otic, local, ventricle, vaginal, rectal, dermal, intravenous, intramuscular, subcutaneous and intradermal route.

The invention claimed is:

1. An antiviral composition which is effective on Herpes Simplex Virus (HSV) comprising a mixture of:
   a glycerin-water-chlorhexidine mixture, a carbopol, NaOH solution, a boron compound and a poloxamer;
   wherein the boron compound is sodium pentaborate pentahydrate;
   wherein the antiviral composition is applied at a level of 0.0005% (w/v) chlorhexidine without cytotoxicity;
   wherein the glycerin-water-chlorhexidine mixture comprising 3% (vol) glycerin and chlorhexidine, wherein a concentration of the chlorhexidine is from 0.12 g/mL to less then 0.2 g/mL;
   wherein the carbopol is added into the glycerin-water-chlorhexidine mixture to prepare a carbopol solution with a concentration of 1% (w/v);

wherein the NaOH solution is added into the carbopol solution to enable gelation of the carbopol and to neutralize pH;

wherein the carbopol solution is hydrated in the glycerin chlorhexidine mixture at room temperature;

wherein the boron compound is added into the carbopol solution;

wherein the poloxamer is added into the carbopol solution.

2. The antiviral composition according to claim 1, wherein a content of the boron compound in the antiviral composition is 0.5-5% (w/v).

3. The antiviral composition according to claim 1, wherein a content of poloxamer in the antiviral composition is 0.3-5% (w/v).

4. The antiviral composition according to claim 1, wherein the form of the antiviral composition is selected from a group consisting of tablet, capsule, pastille, drops, syrup, suppository, gel, and lotion.

5. The antiviral composition according to claim 1, wherein the antiviral composition is administered by a way that enable body absorption, the way is selected from a group consisting of oral, nasal, ophthalmic, otic, local, ventricle, vaginal, rectal, dermal, intravenous, intramuscular, subcutaneous and intradermal route.

6. The antiviral composition according to claim 1, wherein the antiviral composition comprises 300 µg/ml sodium pentaborate pentahydrate, 0.0005% (w/v) chlorhexidine and 5 mg/ml poloxamer.

* * * * *